July 1, 1941. O. S. HONAKER Plant Pat. 478
CARNATION PLANT
Filed Feb. 10, 1941
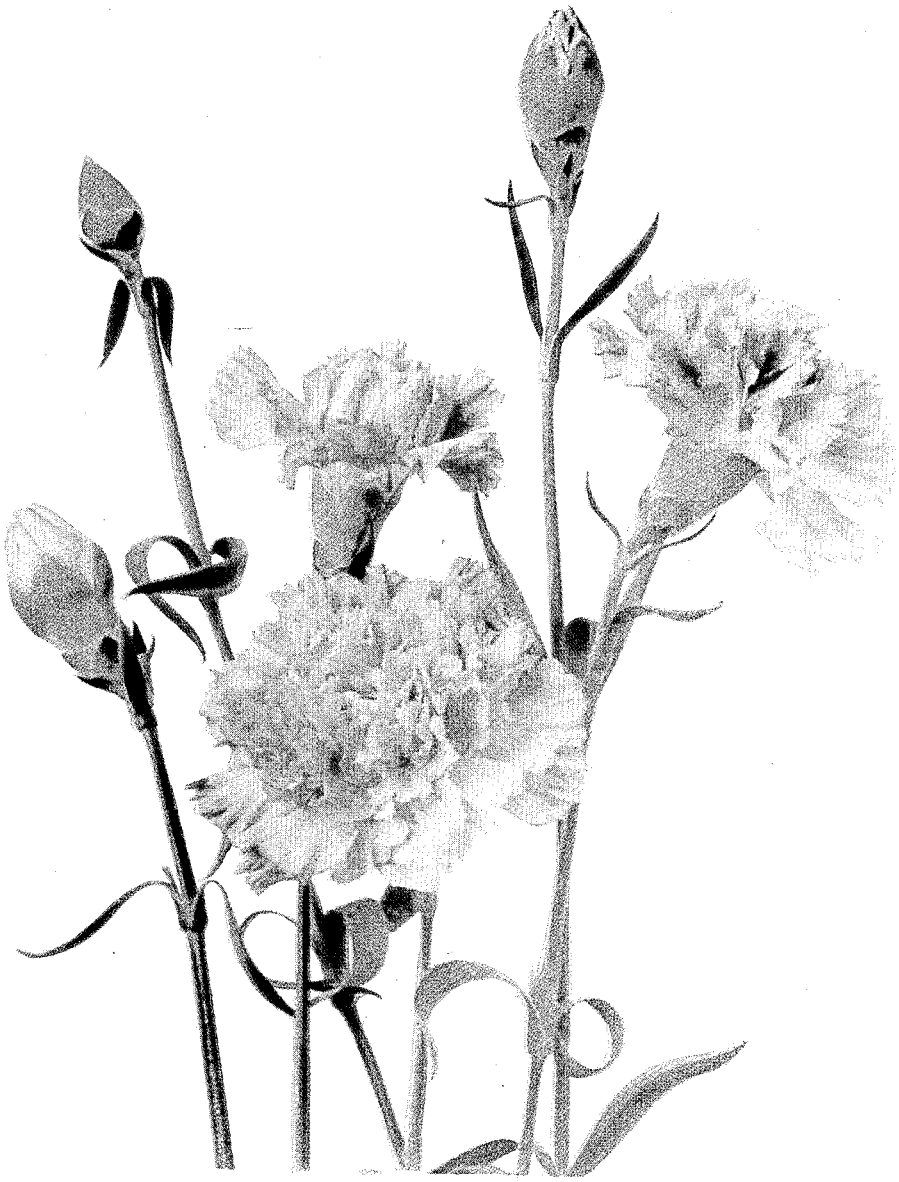
Inventor
O. S. Honaker
By Robb & Robb
Attorneys Patented July 1, 1941

UNITED STATES PATENT OFFICE

478

CARNATION PLANT

Ollie S. Honaker, Lexington, Ky.

Application February 10, 1941, Serial No. 378,293

1 Claim. (Cl. 47—60)

The present invention relates to a new and distinct variety of carnation plant, the result of a definite effort to produce a characteristically new type of flower having reference to varieties of carnation at present well known.

The objective has been realized in the attainment herein set forth, in that this carnation possesses a very desirable color with excellent growth characteristics not represented in production at the present time. Perhaps, the nearest of old or known varieties similar to the present is "Patrician," one of its parents, the similarity residing primarily however in the growth characteristic, but differing therefrom essentially in productivity and color of blossom.

More specifically, the present carnation is very prolific, produces large, full flowers of a very pleasing shade of rose and on very stiff and erect stems. One of its interesting distinctions resides in the fact that rarely, if ever, does its calyx split, and I find it further a good producer of cuttings and disease resistant.

With these dominating features of novelty in mind, I now set forth a more detailed description, in which color terminology refers to Ridgway's Color Standard:

Type: Tall; greenhouse; seedling; for cut flowers.

Breeding or discovery: Seedling.

*Seed parent.*—Patrician.

*Pollen parent.*—King Cardinal.

*Propagation:* By cuttings.

*Flower*

Locality where grown: In greenhouses at Lexington, Kentucky.

Bud:

*Color of bud while tight before calyx breaks.*—Calliste Green near base; Peacock Green and Parrot Green on toward tip (Plate VI).

*Peduncle.*—Medium length; heavy; erect; medium smooth; few in number.

*Flowers borne.*—Three to stem in irregular clusters, on strong, medium length stems. In greenhouse it is customarily disbudded to single bloom her stem.

*Before calyx breaks.*—*Size*—medium. *Form*—without foliaceous appendages on the surface of the bud, and without foliaceous parts extending beyond the tip of the bud; ovate, pointed tip.

*As calyx breaks.*—*Color*—Tyrian Rose, Plate XII.

*As first petal opens.*—*Size*—large. *Form*—obovate. *Color:* outside—Tyrian Rose tip, shading through Rose Red to Rose Color toward base. More Rose Color than Rose Red (Plate XII). Inside—Tyrian Rose tip, shading through Rose Red to Rose Color toward base (Plate XII).

*Opening.*—Bud opens up well.

Quantity of bloom: Abundant in greenhouse.

Continuity: Continuous.

Fragrance: Penetrating.

Bloom:

*Size, when fully open.*—Large, 3¼ to 3½ inches.

*Petalage.*—Very double; from 64 to 77 petals, arranged regularly.

*Form.*—Full high center at first and remaining so; petals remaining at first tightly rolled outward, and remaining at maturity tightly rolled outward.

Petals: Thick with inside and outside satiny.

*Shape.*—outside—obovate with long tapering base; scalloped with apex flat with variably one, two or three notches. *Intermediate*—obovate with long tapering base; scalloped with apex flat with variably one, two or three notches.

*Inside*—oblanceolate; irregular with apex flat with variably one, two or three notches.

*Color.*—General color of bloom—Rose Color, Plate XIII.

This description of a newly opened flower was made from a carnation grown in a greenhouse in January, 1941, at Lexington, Kentucky;

*Color.*—Outside petal: outside surface—Rose Color, tip Tyrian Rose, Plate XII; inside surface—Rose Red, tip Tyrian Rose, Plate XII. Intermediate petal:—Outside surface—Rose Color, tip Tyrian Rose, Plate XII; inside surface—Rose Red, tip Tyrian Rose, Plate XII. Inner petal:—outside surface—Rose Color; inside surface—Rose Color.

This description was made from a carnation that was open for three days in a greenhouse in January, 1941, at Lexington, Kentucky:

*Color.*—Outside petal:—outside surface—Rose Color; inside surface—Rose Color, Inside petal:—outside surface—Rose Color; inside surface—Rose Color, General color effect:—newly opened flower—Rose Color, Plate XII; three days open—Rose Color, Plate XII. *Behavior*—persist. *Flower longevity*—cut flower grown in greenhouse kept at living room temperature, ten days.

*Reproductive organs*

Stamens: Few, arranged irregularly about pistils.
Filaments:—Long; White; with anthers.
Anthers: Very small; open at various times; Lemon Yellow.
Pollen: Very sparse; Yellow.
Pistils: Two.
Styles: Uneven; very long; heavy; separated.
Stigma: White.
Ovaries: All enclosed in calyx.
Hips: With inconspicuous neck, pear-shaped; smooth; walls thick.
*Color.*—Grape Green, Plate XLI.
Sepals: Permanent; moderately long; straight.
*Color.*—Calliste Green and Peacock Green, Plate VI.
Seed: Many; medium size.

*Plant*

Foliage: Leaves abundant; large; leathery; no leaflets.
*Color.*—Mature—upper surface—Dusky Yellowish Green, Plate XLI; under surface—Dusky Olive Green, Plate XLI. Young—upper surface—Spinach Green, Plate V; under surface—Asphodel Green, Plate XLI.
*Disease.*—Resistant to rust and stem rot.
Growth:
*Habit.*—Upright, vigorous.
*Growth.*—Vigorous.
*Canes.*—Heavy.
*Main stems.*—Leaf Green, Plate XLI.
*Branches.*—Lettuce Green, Plate V.
*New shoots.*—Pale Cendre Green, Plate VI.

I claim:

A new and distinct variety of carnation plant characterized as to novelty by its productive habit of growth, prolificacy of large, full flowers, the unusual rose color of said flowers, the absence of splitting of the calyx; the excellent production of cuttings, the production of flowers upon very stiff and erect stems, and its resistance to disease, substantially as shown and described.

OLLIE S. HONAKER.